(12) United States Patent
Cho (10) Patent No.: US 11,504,012 B2
(45) Date of Patent: Nov. 22, 2022

(54) DIAPHRAGM-BASED SENSOR WITH A CORRUGATED SIDEWALL

(71) Applicant: University of Pittsburgh-Of the Commonwealth System of Higher Education, Pittsburgh, PA (US)

(72) Inventor: Sung Kwon Cho, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 399 days.

(21) Appl. No.: 16/749,247

(22) Filed: Jan. 22, 2020

(65) Prior Publication Data

US 2020/0281481 A1 Sep. 10, 2020

Related U.S. Application Data

(60) Provisional application No. 62/797,002, filed on Jan. 25, 2019.

(51) Int. Cl.
*A61B 5/0215* (2006.01)
*B81B 3/00* (2006.01)
*B81C 1/00* (2006.01)

(52) U.S. Cl.
CPC .......... *A61B 5/0215* (2013.01); *B81B 3/0021* (2013.01); *B81C 1/00158* (2013.01); *A61B 2562/125* (2013.01); *B81B 2201/0264* (2013.01); *B81B 2203/0127* (2013.01); *B81B 2203/0315* (2013.01)

(58) Field of Classification Search
CPC ............ A61B 5/0215; A61B 2562/125; A61B 2560/0223; A61B 2562/0204; A61B 2562/0257; A61B 2562/029; A61B 2562/12; B81B 3/0021; B81B 2201/0264; B81B 2203/0127; B81B 2203/0315; B81B 3/007; B81C 1/00158; G01L 9/0048
See application file for complete search history.

(56) References Cited

U.S. PATENT DOCUMENTS

| 2004/0246311 | A1* | 12/2004 | Silverbrook | B41J 2/1645 347/57 |
| 2016/0137486 | A1* | 5/2016 | Bharatan | H04R 19/005 257/416 |
| 2022/0110655 | A1* | 4/2022 | Mikol | A61M 13/003 |

(Continued)

OTHER PUBLICATIONS

Chen et al., "Wireless Intraocular Pressure Sensing Using Microfabricated Minimally Invasive Flexible-Coiled LC Sensor Implant," *J. of Microelectromech. Syst.*, vol. 19, No. 4, pp. 721-734, Aug. 2010.

(Continued)

*Primary Examiner* — Douglas W Owens
(74) *Attorney, Agent, or Firm* — Klarquist Sparkman, LLP (57) ABSTRACT

A diaphragm-based sensor includes a deflectable diaphragm, a base layer opposite the diaphragm, and a corrugated wall extending between the diaphragm and the base layer. The diaphragm is suspended over a cavity enclosed by the diaphragm, the base layer and the corrugated wall. The diaphragm includes a first electrode and the base layer includes a second electrode such that a capacitance between the first and second electrodes changes when the diaphragm is deflected relative to the cavity.

20 Claims, 9 Drawing Sheets

(56) References Cited

U.S. PATENT DOCUMENTS

2022/0112540 A1* 4/2022 Weng .................. C12Q 1/6806

OTHER PUBLICATIONS

Eaton et al., "Micromachined Pressure Sensors: Review and Recent Developments," Smart Mater. Struct., vol. 6, pp. 530-539, 1997.
Kim et al., "Parylene-Based Electrochemical-MEMS Force Sensor Array for Assessing Neural Probe Insertion Mechanics," 25$^{th}$ IEEE Intt. Conf. MEMS 2012, Paris, France, Jan. 29-Feb. 2, 2012, pp. 124-127.
Kotake et al., "A Flexible Parylene-based Glutamate Sensor," Proceedings of the 5$^{th}$ International IEEE EMBS Conference on Neural Engineering, Cancun, Mexico, Apr. 27-May 1, 2011, pp. 314-316.
Timoshenko et al., "Theory of Plates and Shells," 2$^{nd}$ edition, McGraw-Hill Classic Textbook Reissue, 591 pages, 1987.

* cited by examiner

DIAPHRAGM-BASED SENSOR WITH A CORRUGATED SIDEWALL

CROSS-REFERENCE TO RELATED APPLICATION

This application claims the benefit of U.S. Provisional Patent Application No. 62/797,002, filed Jan. 25, 2019, which is incorporated herein by reference.

ACKNOWLEDGMENT OF GOVERNMENT SUPPORT

This invention was made with government support under Grant No. W81XWH-16-2-0062 awarded by the Army/MRMC. The government has certain rights in the invention.

FIELD

The present disclosure concerns embodiments of a diaphragm-based sensor with improved structural strength and the methods of fabricating the same.

BACKGROUND

Microfabricated parylene-based implantable sensors have been attractive for medical devices due to their biocompatibility and flexibility. In particular, implantable micro pressure sensors have been developed using parylene and integrated with a miniaturized inductor for wireless pressure reading. Parylene-C can be used in the fabrication of a pressure sensor to create a flexible coil substrate that can be folded for implantation in a patient's body, as well as to create a cavity chamber with a diaphragm (or membrane) suspended over the cavity. For this implantable application, the sensor resolution should be high due to the relatively low-pressure range (0-200 mmHg) within the human body. Thus, it favors a large dimension (e.g., greater than several hundred microns in diameter) for the diaphragm and small gap (e.g., less than tens of microns) between the parallel electrodes located on top and bottom sides of the cavity. The deflection of the diaphragm under pressure is related to the applied pressure. The deflection can be commonly measured capacitively or piezo-resistively.

The deflection of a circular diaphragm due to applied pressure is depicted by $$w(r) = \frac{P(a^2 - r^2)^2}{64D}$$

where w, r, a, P, and D are respectively the deflection, radial distance from the center of the diaphragm, diaphragm radius, applied pressure, and flexural rigidity. The flexural rigidity, D, is given by $$D = \frac{Eh^2}{12(1-v^2)}$$

where E, h, and v are the Young's modulus, thickness of the diaphragm, and Poisson's ratio, respectively. In the capacitive pressure sensor, in particular, one (bottom) electrode is placed on the substrate and the other (top) electrode is placed on the diaphragm. The capacitance, C, between the electrodes is directly related to the degree of diaphragm deflection by $$C = \int\int \frac{\varepsilon}{d - w(r)} r\, dr\, d\theta$$

where ε and d are respectively the permittivity and the separation between the bottom and top electrodes.

Meanwhile, it has been known that there exists difficulty in the formation of a three-dimensional cavity chamber with a large diaphragm suspended over the cavity. These geometrical constraints increase the possibility of diaphragm collapse during fabrication or operation, as well as the inconsistent diaphragm deflection under the change of applied pressure resulting from the degradation of the cavity sidewall. For example, stiction during diaphragm release from a sacrificial photoresist in solvent or intermolecular forces between the diaphragm and a solid substrate may be major causes for collapse. Thus, there is a need for improved structural strength of implantable diaphragm-based sensors and related fabrication process.

SUMMARY

Certain embodiments of the disclosure concern a diaphragm-based sensor.

In one particular embodiment, the diaphragm-based sensor can be a capacitive pressure sensor.

In some embodiments, the sensor can include a deflectable diaphragm, a base layer opposite the diaphragm, and a corrugated wall extending between the diaphragm and the base layer. The diaphragm can be suspended over a cavity defined by the diaphragm, the base layer and the corrugated wall.

In some embodiments, the diaphragm can include a first electrode, and the base layer can include a second electrode such that a capacitance between the first and second electrodes can change when the diaphragm is deflected relative to the cavity. In some embodiments, the corrugated wall can include a plurality of ridges alternating with a plurality of grooves.

In some embodiments, a ratio of a height of the corrugated wall to a diameter of the diaphragm can range from about 0.0005 to about 1.

In some embodiments, the diaphragm can have a diameter about 800 μm.

In some embodiments, the corrugated wall can have a height about 7 μm.

In some embodiments, the first electrode can be encapsulated between at least two parylene layers.

In some embodiments, the second electrode can be encapsulated between at least two parylene layers.

In some embodiments, each of the plurality of ridges can have a rectangle-shaped radial cross-section.

In some embodiments, the rectangle-shaped radial cross-section can have a width about 80 μm and a length about 100 μm.

In some embodiments, two adjacent ridges can form a radial angle about 15 degrees.

In some embodiments, the cavity can be filled with a fluid which has a dielectric constant greater than 1.

In some embodiments, the fluid can include propylene carbonate.

Certain embodiments of the disclosure also concern a method of fabricating a diaphragm-based sensor, such as a capacitive pressure sensor.

In some embodiments, the method can include forming a base layer on a substrate, forming a corrugated wall on the base layer so as to form a cavity, and forming a diaphragm suspended over the cavity and supported by the corrugated wall.

In some embodiments, the diaphragm can include a first electrode and the bottom layer can include a second electrode such that a capacitance between the first and second electrodes can change when the diaphragm is deflected relative to the cavity.

In some embodiments, the cavity can be formed by removing a sacrificial photoresist layer deposited between the diaphragm and the base layer.

In some embodiments, the sacrificial photoresist layer can be patterned to have a body portion having a corrugated side surface.

In some embodiments, the method can further include filling the cavity with a fluid that has a dielectric constant greater than 1.

In some embodiments, filling the cavity with the fluid can include submerging the base layer, the corrugated wall, and the diaphragm into a pool of the fluid for a predefined duration.

In some embodiments, the method can further include sealing the cavity.

The foregoing and other objects, features, and advantages of the invention will become more apparent from the following detailed description, which proceeds with reference to the accompanying figures.

DETAILED DESCRIPTION

Described herein are examples of an improved diaphragm-based sensor and methods of fabricating the same. Although a capacitive pressure sensor is described below as a representative example, it should be understood that the improved sensor structure design disclosed herein can be used in any type of sensor that incorporates a flexible diaphragm, such as a piezoelectric sensor. Further, the sensor can be used to detect and measure various other metrics such as proximity, position, displacement, acceleration, force, humidity, fluid level, sound level, bio molecules, etc. For example, the improved diaphragm-based sensor disclosed herein can be an implantable blood pressure sensor, a micro proximity sensor, a capacitive microphone, etc.

Figure 1A:
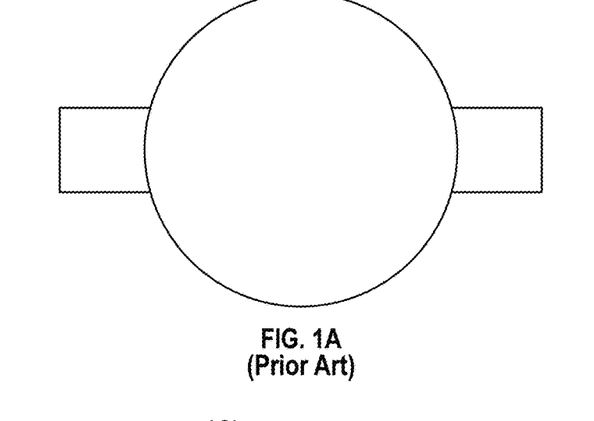
FIG. 1A is a schematic depiction of a top plan view of a conventional capacitive pressure sensor.
Figure 1B:
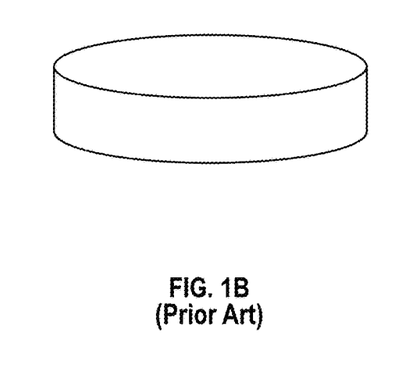
FIG. 1B is a perspective view of the conventional capacitive pressure sensor depicted in FIG. 1A.

Conventionally, it is challenging to fabricate a three-dimensional capacitive cavity chamber with a large diaphragm (e.g., about 800 μm in diameter or larger) suspended over the cavity on the substrate (see, e.g., FIGS. 1A-1B). Specifically, the strength of the sidewall supporting the diaphragm is prone to collapse. Although one option to increase the structural rigidity of the device is to increase the thickness of the sidewall, this is not easily achievable via conventional deposition methods because depositing a thicker layer for the sidewall can also increase the thickness of the diaphragm, which in turn can result in decreased flexibility of the diaphragm and reduced resolution of pressure measurement.

Figure 2A:
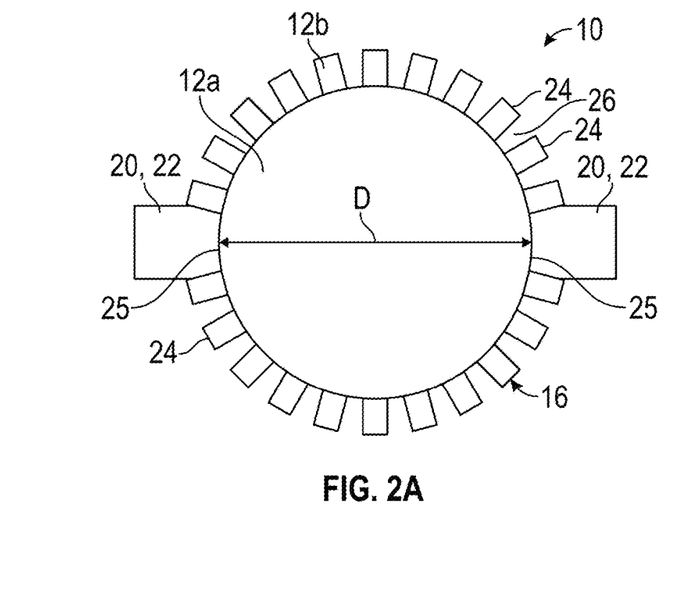
FIG. 2A is a schematic depiction of a top plan view of an improved capacitive pressure sensor, according to one embodiment.
Figure 2B:
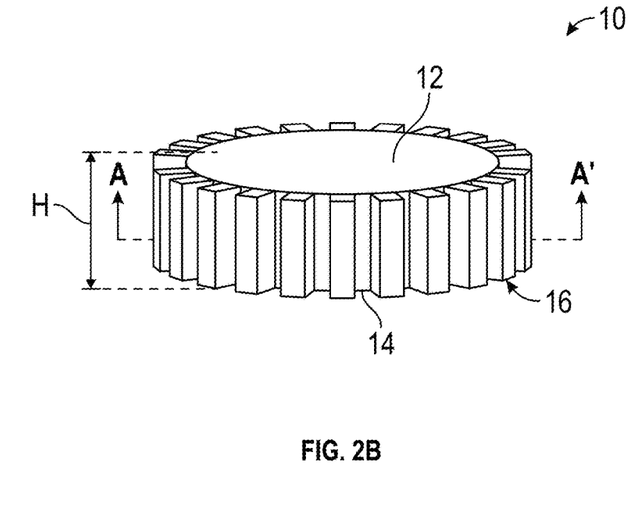
FIG. 2B is a perspective view of the capacitive pressure sensor depicted in FIG. 2A.
Figure 2C:
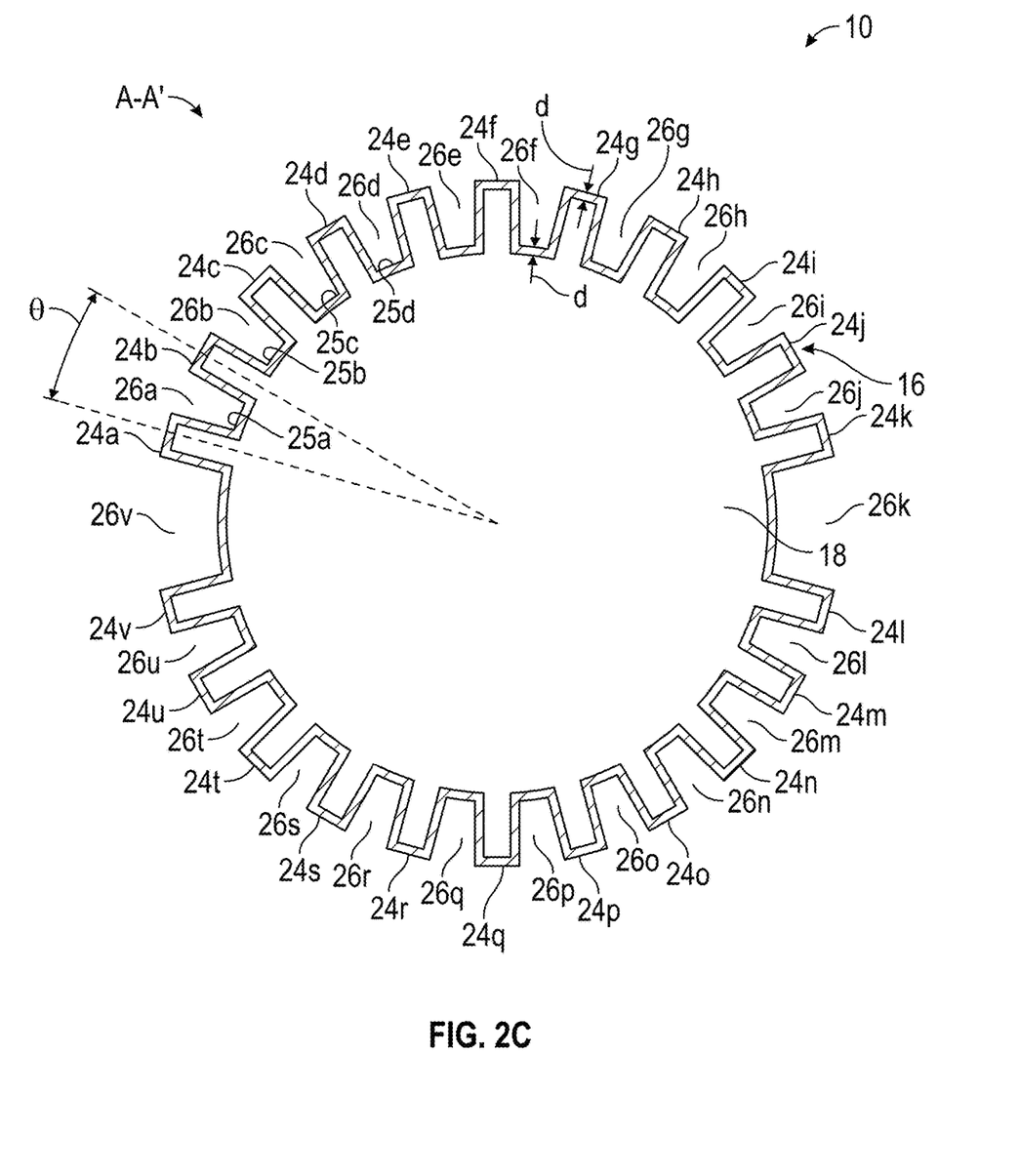
FIG. 2C is a cross section of the capacitive pressure sensor depicted in FIG. 2A taken along line A-A' of FIG. 2B.

FIGS. 2A-2C show an improved capacitive pressure sensor 10 with increased structural rigidity, according to one embodiment. As shown, the improved capacitive pressure senor 10 includes a deflectable diaphragm 12, a base layer 14 opposite the diaphragm, and a corrugated wall 16 extending from the diaphragm 12 to the base layer 14. The diaphragm 12 is suspended over a cavity 18 enclosed by the diaphragm 12, the base layer 14 and the corrugated wall 16 (also referred to as the "corrugated sidewall").

In some embodiments, the cavity 18 can be filled with a fluid having a high-dielectric constant, which can increase the range of capacitance measured between the diaphragm 12 and the base layer 14 and thus the sensitivity for pressure measurement. For example, compared to filling the cavity 18 with air whose dielectric constant is 1.0, filling the cavity 18 with propylene carbonate whose dielectric constant is about 64 can increase the sensitivity of pressure measurement by about 64 fold.

The diaphragm 12 can include a first metal plate 20 (also referred to as the "top plate"), and the base layer can include a second metal plate 22 (also referred to as the "bottom plate"). For clarity, the first and second metal plates 20, 22 are not shown in FIG. 2B. The first and second metal plates 20, 22 can function as a pair of capacitance-sensing electrodes such that when the diaphragm 12 is deflected relative to the cavity 18, a corresponding change in capacitance between the first and second metal plates 20, 22 can be detected by an electronic circuit connecting to the first and second metal plates 20, 22. In some embodiments, the top plate 20 covers an entire area of the diaphragm 12 and the bottom plate 22 covers an entire area of the base layer 14. In other embodiments, the top plate 20 covers only a portion of the diaphragm 12 and the bottom plate 22 covers only a portion of the base layer 14.

In the depicted embodiment, the diaphragm 12 and the base layer 14 are about the same size (e.g., the diaphragm and the base layer can have the same diameter). In other embodiments, the diaphragm 12 and the base layer 14 can differ in sizes (e.g., the diaphragm and the base layer can have different diameters). For example, the base layer 14 can be larger or smaller than the diaphragm 12.

In the depicted embodiment, the diaphragm 12 and the base layer 14 are substantially circular except at the peripheral region such that the cavity 18 has a substantially cylindrical shape except for having a corrugated sidewall. In other embodiments, the diaphragm 12 and the base layer 14 can have other shapes, such as oval, polygonal, etc. In alternative embodiments, the shape of the diaphragm 12 can be different than that of the base layer 14.

A radial dimension (D) of the diaphragm 12 can be measured as the maximum dimension of the diaphragm in the radial plane excluding the corrugated edge portion. For example, in the embodiment depicted in FIG. 2A, the diaphragm 12 has a generally circular inner portion 12a and a corrugated edge portion 12b, and the radial dimension (D) of the diaphragm can be defined as the diameter of the circular inner portion 12a. The corrugated edge portion 12b is comprised of a plurality of ridges 24 and grooves 26 (discussed below) and circular arcs 25 extending between adjacent ridges. Thus, the radial dimension (D) is the length of a line that extends between diametrically opposed locations on circular arcs 25 of the diaphragm. In some embodiments, a ratio between a height (H) of the corrugated wall 16 and the radial dimension (D) of the diaphragm 12 can range from about 0.0005 to about 1. In some embodiments, the H:D ratio can range from about 0.01 to about 2.

In some embodiments, the maximum radial dimension (D) of the diaphragm 12 can range from about 10 μm to about 3000 μm. In some embodiments, D can range from about 1 μm to about 1000 μm. In one particular embodiment, D can be about 800 μm.

In some embodiments, the height (H) of the corrugated wall 16 can range from about 0.1 μm to about 50 μm. In some embodiments, H can range from about 1 μm to about 100 μm. In one particular embodiment, H can be about 7 μm.

In the depicted embodiment, the corrugated wall 16 includes a plurality of ridges 24 (e.g., 24a, 24b, 24c, 24d, etc.) alternating with a plurality of grooves 26 (e.g., 26a, 26b, 26c, 26d, etc.) and a plurality of arcs 25 (e.g., 25a, 25b, 25c, 25d, etc.) extending between adjacent ridges 24. The number of ridges 24 and grooves 26 can vary. For example, the number of ridges 24 and grooves 26 can vary from 2 to more than 20 (e.g., 22 pairs of ridges and grooves are depicted in FIG. 2C).

In the depicted embodiment, the corrugated cross-sectional profile formed by the ridges 24 and grooves 26 extends into the diaphragm 12 such that the edge portion 12b of the diaphragm has the same cross-sectional profile (in a plane parallel to the dimension D and perpendicular to height H) as the corrugated wall 16. Therefore, the reference numerals 24, 25, and 26 can be used to refer to the ridges, arcs, and grooves, respectively, in any cross-sectional plane (parallel to the dimension D and perpendicular to height H) extending through the wall 16 or the diaphragm 12

In some embodiments, the plurality of ridges 24 and the grooves 26 can be spaced apart from each other uniformly around the outer periphery of the sensor 10. In other embodiments, the plurality of ridges 24 and the grooves 26 can be spaced apart from each other non-uniformly around the outer periphery of the sensor 10.

In further embodiments, the plurality of ridges 24 and the grooves 26 can be spaced apart from each other uniformly around one or more selected portions, but non-uniformly in other portion of the periphery of the sensor 10. For example, in the embodiment depicted in FIG. 2C, one group of ridges (24a-24k) and the associated grooves (26a-26j) are uniformly distributed on one side of the sensor, another group of ridges (24l-24v) and the associated grooves (26l-26u) are uniformly distributed on the opposite side of the sensor, whereas two grooves (26k and 26v) that are relatively larger than the rest of the grooves separate the aforementioned two groups of ridges.

In the depicted embodiments, each of the plurality of ridges 24 extends from the base layer 14 to the diaphragm 12. In other words, the axial length of the ridges 24 equals the height (H) of the corrugated wall 16. In other embodiments, at least some of the ridges can extend only a portion of the corrugated wall 16. In other words, the axial length of the ridges can be smaller than H. For example, some of the ridges can have an axial length that is between about 20% to about 90% of H.

In the depicted embodiment, each of the plurality of ridges 24 has a rectangle-shaped radial cross-section. For example, in some embodiments, the rectangle-shaped radial cross-section can have a width (W) ranging from about 1 μm to about 500 and the length (L) ranging from about 1 μm to about 500 In some embodiments, W can range from about 10 µm to about 100 and L can range from about 10 µm to about 150 In one particular embodiment, W can be about 80 µm and L can be about 100 In the illustrated embodiment, all of the ridges 24 are the same size in cross section. In other embodiments, either the width (W) and/or the length (L) dimensions can vary from ridge to ridge.

In other embodiments, the radial cross-section of the ridges can have other shapes, such as triangle, trapezoid, etc. In some embodiments, the radial cross-section of at least some of the ridges can progressively increase or decrease in width in the radial direction. For example, in certain embodiments, the outer edge 25a of a ridge can be wider than the inner foot area 25b of the ridge. In other embodiments, the outer edge 25a of the ridge can have a curved shape. In still other embodiments, one or both lateral sides of the ridges 25c can have a curved shape. In the illustrated embodiment, the width (W) of the ridges is generally uniform in the axial direction. In other embodiments, the width (W) of the ridges can vary along the axial direction. As shown in FIGS. 2A-2C, any one of the grooves 26 is located between two adjacent ridges 24. Thus, the dimensions of the grooves 26 (e.g., width and depth) can be determined by the corresponding dimensions of its adjacent ridges 24. As shown, the radial axes of two adjacent ridges 24 can form an angle θ. The angle θ can be dependent on the number of ridges 24. For example, when the corrugated wall has only two ridges located at the diametrically opposite sides of the diaphragm 12, the angle θ can be 180°. In some embodiments, the angle θ can vary between about 1° and about 180°. In the depicted embodiments, the angle θ is about 15°. In some embodiments, the angle θ can vary around the periphery of the sensor, for example, when the ridges are spaced apart from each other non-uniformly.

In some embodiments, the thickness (d) of the corrugated wall 16 can be substantially uniform across the plurality of ridges 24 and grooves 26. In other embodiments, the thickness (d) of the corrugated wall 16 can vary between the plurality of ridges 24 and grooves 26. In certain embodiments, the thickness (d) of the corrugated wall 16 can range from about 0.1 µm to about 50 µm. In some embodiments, the thickness (d) of the corrugated wall 16 can range from about 1 µm to about 15 By introducing corrugations to the sidewall 16 of the sensor 10 supporting the diaphragm 12, stiffness of the sidewall 16 is increased (for example, when compared to a conventional capacitive pressure sensor having a non-corrugated sidewall with similar wall thickness d).

In the depicted embodiments, each of the first and second metal plates 20, 22 is substantially encapsulated within insulating layers. For example, each of the first and second metal plates 20, 22 can be sandwiched between at least two insulating layers. Each of the first and second plates 20, 22 can be connected to an electronic circuit (not shown) by one or more wires which can also be substantially insulated by an insulation layer. Any suitable electrical insulating material can be used for the insulation layer.

For implantable sensors, biocompatible insulating material can be used for the insulating layer, such as parylene. In the following, parylene is described as an exemplary embodiment for the insulating material although it should be understood that other insulating material may be used depending on applications.

FIG. 3A-3E illustrates one embodiment of a process of fabricating the improved capacitive sensor disclosed above.

Figure 3A:
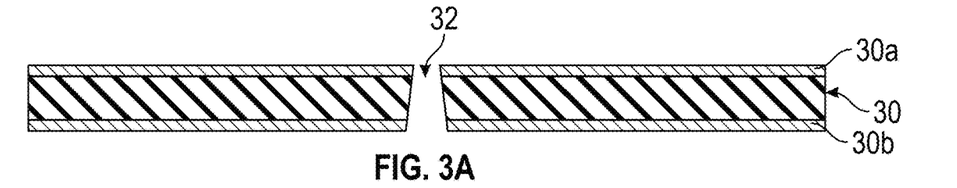
FIG. 3A illustrates one step of a process for fabricating an improved capacitive pressure sensor, according to one embodiment.

FIG. 3A shows a substrate 30 on which the sensor can be fabricated. In one embodiment, the substrate 30 is a double-side-polished silicon wafer with thermally grown silicon oxide (SiO2) layers 30a, 30b. In one exemplary embodiment, a 300-µm-thick silicon wafer can be used for this sensor fabrication, and the SiO2 masking layers 30a, 30b can have a thickness about 2 µm. In one embodiment, the $SiO_2$ masking layer 30a can be patterned by wet-etching using a buffered hydrofluoric (BHF) acid solution and a photoresist mask, followed by the conventional KOH silicon backside etching. As shown in FIG. 3A, the silicon wafer 30 can be fully etched to the front surface to form an open window 32. In one exemplary but non-limiting embodiment, the size of the open window 32 can be about 20 µm×20 µm.

Figure 3B:
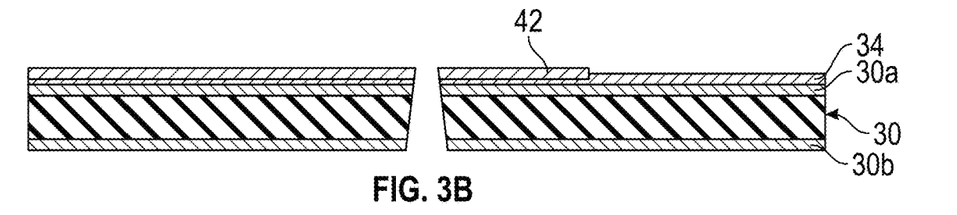
FIG. 3B illustrates another step of the process for fabricating the capacitive pressure sensor, according to one embodiment.

As shown in FIG. 3B, a parylene layer 34 can be coated on the silicon oxide layer 30a. In one exemplary but non-limiting embodiment, the parylene layer 34 can have a thickness of about 5 µm. The parylene layer 34 can be baked, e.g., for about 6 hours at about 150° C. to increase the adhesion of parylene layer 34 to the surface 30a.

Still referring to FIG. 3B, a metallic layer 42 can be patterned for forming the bottom plate 22 of the capacitive pressure sensor 10. In some embodiments, the metallic layer 42 can have a circular shape, although other shapes can also be patterned.

Figure 3C:
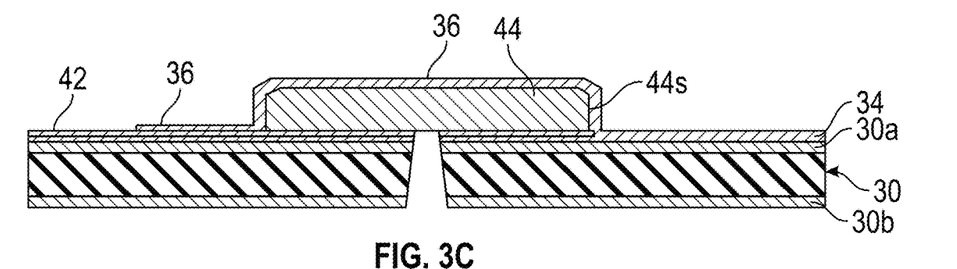
FIG. 3C illustrates yet another step of the process for fabricating the capacitive pressure sensor, according to one embodiment.

As shown in FIG. 3C, on the surface of the bottom metallic plate 42, a sacrificial photoresist (PR) layer 44 can be patterned. As described below, the size and shape of the sacrificial PR layer 44 determines the size and shape of the cavity 18 of the sensor 10. For example, to create a substantially cylindrically shaped cavity with a radial diameter of 800 µm and a height about 7 µm, the sacrificial PR layer 44 is also patterned to have a substantially cylindrical shape with a radial diameter of 800 µm and a height about 7 µm. In one exemplary but non-limiting embodiment, AZ series photoresist (AZ P4620) can be used in this step for the thick sacrificial PR layer patterning.

In particular, to create the corrugated wall 16, the sacrificial PR layer 44 can be patterned to have a body portion having a corrugated side surface 44s. For example, the corrugated side surface 44s of the sacrificial PR layer 44 can include a plurality of ridges and grooves (not shown) that respectively match the corresponding grooves 26 and ridges 24 of the corrugated wall 16 of the resulting sensor 10.

Figure 3D:
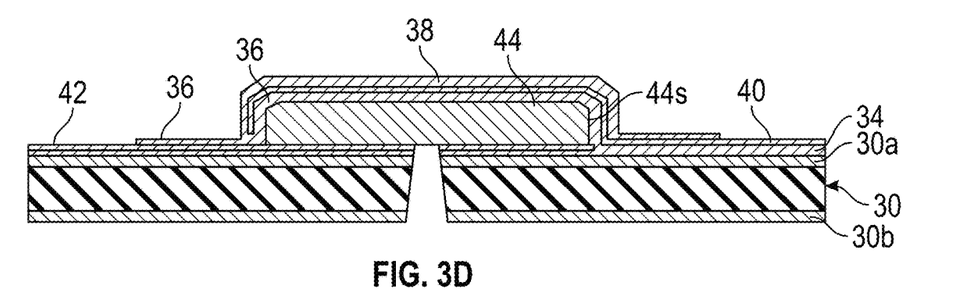
FIG. 3D illustrates a further step of the process for fabricating the capacitive pressure sensor, according to one embodiment.

As shown in FIG. 3D, another metallic layer 40 can be patterned for forming the top plate 20 of the capacitive pressure sensor 10. In some embodiments, multiple parylene layers can be coated to create the flexible sandwich-like-structured diaphragm 12. For example, FIG. 3D shows that the metallic layer 40 can be encapsulated between parylene layers 36 and 38. Likewise, the metallic layer 42 can be encapsulated between parylene layers 36 and 34. In some embodiments, the wires connecting the metallic layers 40, 42 to an electrical circuit can be substantially coated with parylene. In one exemplary but non-limiting embodiment, the overall thickness of parylene layers 36, 38 and the metallic layer 40 for the diaphragm 12 can be about 14 µm and 500 nm, respectively.

Figure 3E:
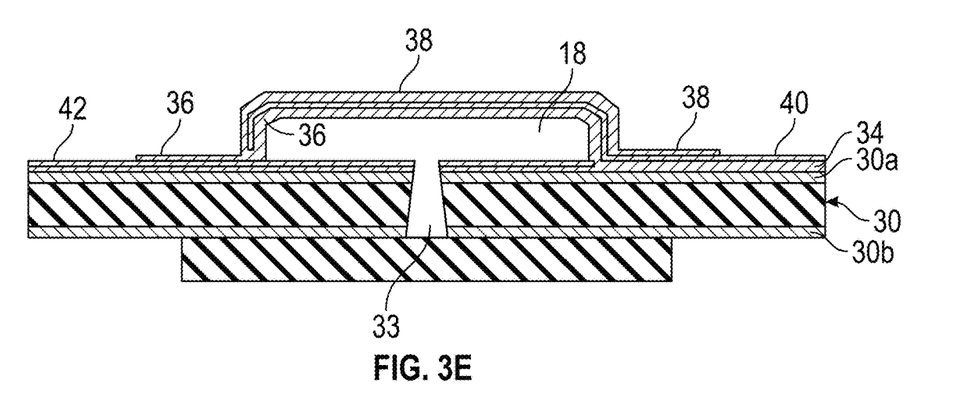
FIG. 3E illustrates yet a further step of the process for fabricating the capacitive pressure sensor, according to one embodiment.

As shown in FIG. 3E, the cavity 18 can be formed by removing the sacrificial PR layer 44, for example, by applying an acetone solution to dissolve the sacrificial PR layer 44. After the sacrificial PR layer 44 is fully dissolved, the cavity 18 can be dried by heat and/or air. Thus, the sacrificial PR layer 44 can effectively function as a mold for the cavity 18 of the resulting sensor 10.

As shown in FIG. 3E, after the sacrificial PR layer 44 is removed, the backside etch hole 33 can be sealed to create a cavity or chamber 18 that is isolated or sealed from fluid (e.g., blood) surrounding the sensor. In other embodiments, depending on the application, the backside etch hole 33 may not be sealed such that the cavity 18 is not sealed, thereby allowing the fluid surrounding the sensor to enter the cavity. For example, a sensor with a sealed cavity can be used to measure an absolute external pressure applied to the diaphragm, whereas a sensor with an unsealed cavity can be used to measure the external pressure applied to the diaphragm relative to the internal pressure caused by a fluid filling the cavity.

In some embodiments, the cavity or chamber 18 can be filled with a fluid having a dielectric constant greater than one. One example fluid is propylene carbonate (a liquid) whose dielectric constant is about 64. Other fluids with relatively high-dielectric constants (compared to air) can also be used to fill the cavity 18, such as propylene glycol (with a dielectric constant about 32), ethylene glycol (with a dielectric constant about 37), etc.

In an example embodiment, after removing the sacrificial PR layer 44 using acetone, the entire "chip" (including the substrate 30 and various layers deposited thereon) can be submerged into a pool of a high-dielectric constant liquid (e.g., propylene carbonate) for a predefined duration, which can range from one or more hours to several days. Through diffusion, any residual acetone can be completely replaced by the dielectric fluid. Thereafter, the backside etch hole 33 can be sealed as previously described.

As noted above, filling the cavity 18 with a high-dielectric constant fluid can increase the sensitivity of the pressure sensor measurement by a factor that is equal to the dielectric constant of the filling fluid. For example, the capacitance signal measured by a pressure sensor whose cavity is filled with propylene carbonate can be 64 times higher than a pressure sensor whose cavity is filled with air.

The etching and depositing operations described above can be performed by any known techniques. For example, a reactive ion etch (Trion Phantom III LT RIE) system can be used to etch the parylene layer on the bottom and top plates for the open electrodes. A CVD (chemical vapor deposition) system (PDS 2010, Specialty Coating System Inc.) can be used to deposit a parylene C layer. The metallic layer can be deposited by an e-beam evaporator (Plassys Electron Beam Evaporator MEB550S).

In some embodiments, a plurality of sensors 10 can be formed on the same substrate 30 or on different substrates and can be electrically connected to each other. For example, multiple pressure sensors 10 can be formed on the same or different substrate and can be electrically connected in parallel to increase the overall capacitance and thus the sensitivity for pressure measurement.

More generally, a plurality of diaphragm-based sensors (e.g., pressure sensors or other types of sensors) can be formed on the same substrate or different substrates and can be electrically coupled to each other.

As noted above, the sensor 10 can be a pressure sensor. In particular embodiments, the sensor 10 can be an implantable blood pressure sensor. In certain embodiments, one or more blood pressure sensors 10 can be incorporated in or mounted on another implantable device that is implantable in a patient's body. For example, one or more blood pressure sensors 10 can be mounted on a stent, a stent graft, a prosthetic valve, or any of various other implantable devices. In one specific example, one or more blood pressure sensors 10 can be mounted on an implantable perfusion device as disclosed in U.S. Publication No. 2016/0157868, which is incorporated herein by reference, for measuring the blood pressure in the vessel (e.g., the aorta) in which the perfusion device is implanted.

Figure 4A:
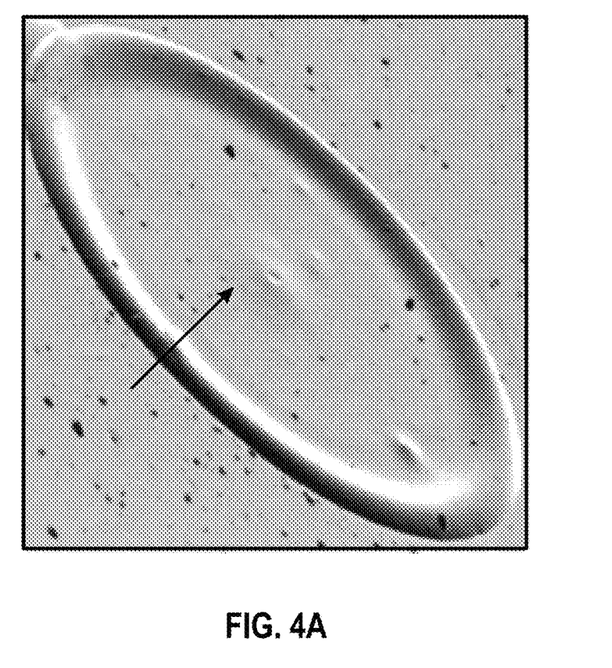
FIG. 4A is a scanning electron microscope image showing a collapsed diaphragm of a conventional capacitive pressure sensor.
Figure 4B:
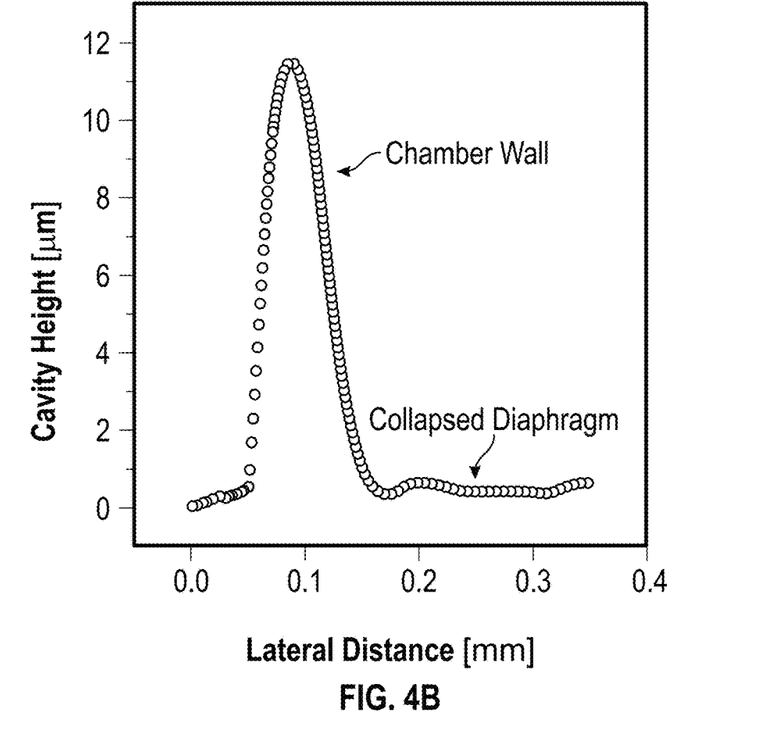
FIG. 4B is a line scanning profile of the conventional capacitive pressure sensor depicted in FIG. 4A.
Figure 5A:
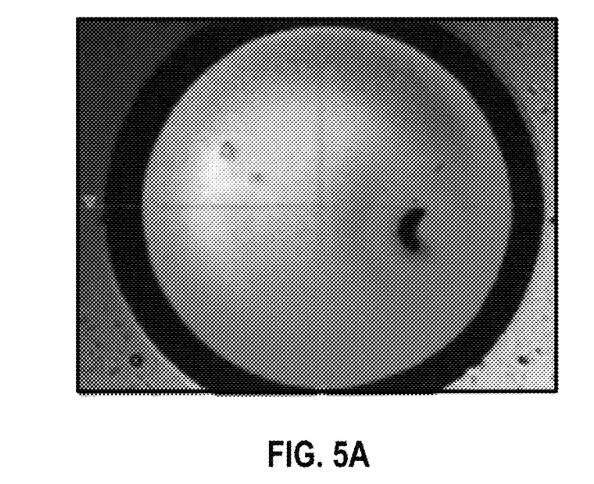
FIG. 5A is a top view of an optical image depicting the diaphragm deflection behavior of a conventional capacitive pressure sensor.
Figure 5B:
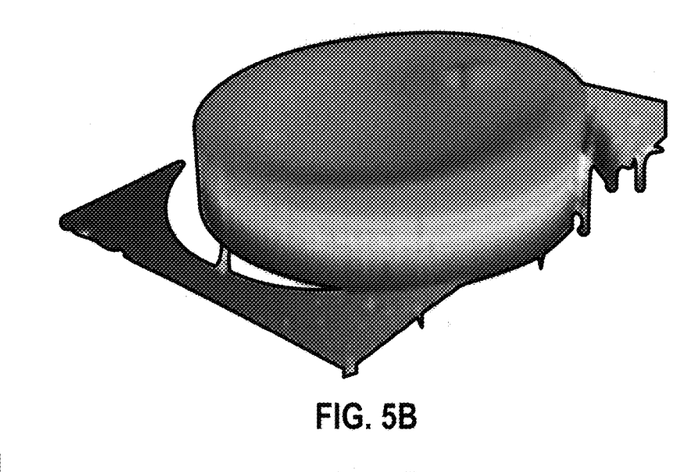
FIG. 5B is a perspective view of the optical image depicted in FIG. 5A.
Figure 5C:
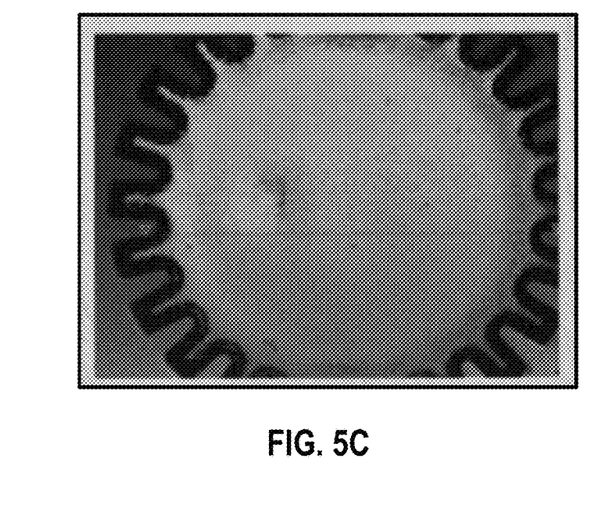
FIG. 5C is a top view of an optical image depicting the diaphragm deflection behavior of an improved capacitive pressure sensor, according to one embodiment.
Figure 5D:
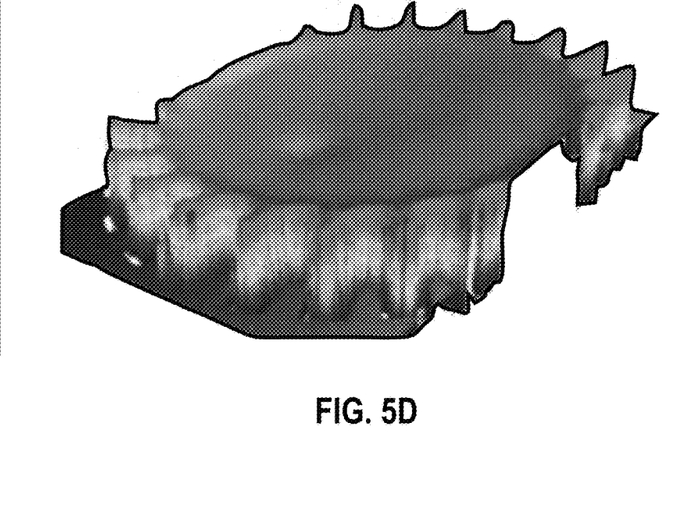
FIG. 5D is a perspective view of the optical image depicted in FIG. 5C.

To further illustrate the disadvantage of conventional capacitive pressure sensors, FIG. 4A shows a scanning electron microscope (SEM) image showing the collapsed diaphragm of one conventional capacitive pressure sensor with a plain cylindrical capacitive cavity chamber (note that the sensor without a corrugated wall can be fabricated using a similar procedure as depicted in FIGS. 3A-3E except that the sacrificial PR layer is patterned with a smooth side surface instead of a corrugated side surface), and FIG. 4B is the line profile measured by a surface profiler. During fabrication of such capacitive sensor, it has been found that the diaphragm can collapse easily at the time of the removal of sacrificial PR in acetone and is not restored even after drying. The non-corrugated wall enclosing the cavity chamber and supporting the large diaphragm is determined to be not strong enough to preserve the cavity chamber from the stiction problem.

Figure 6:
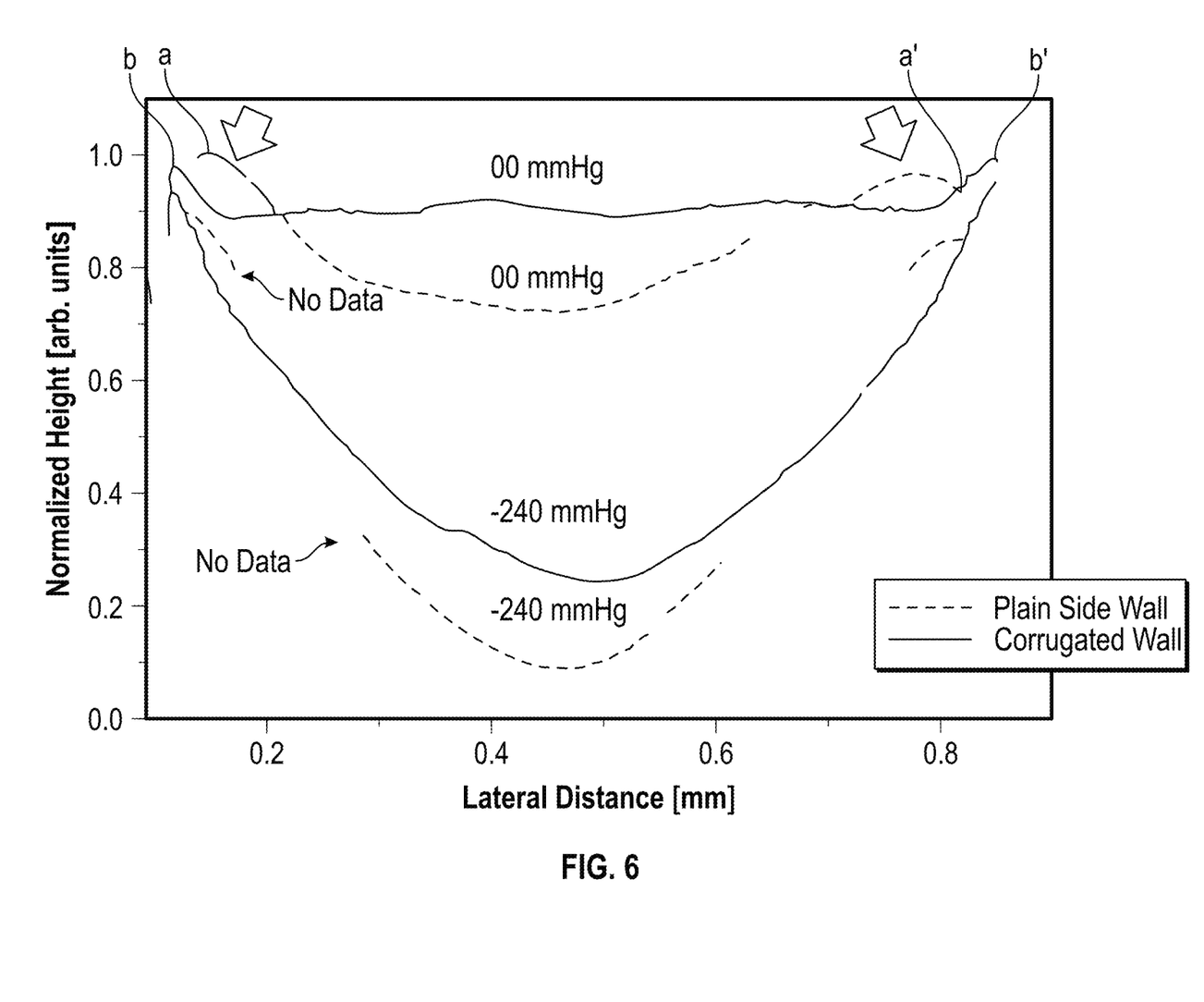
FIG. 6 is a plot comparing the diaphragm deflection behavior between the traditional capacitive pressure sensor depicted in FIGS. 5A-5B and the improved capacitive pressure sensor depicted in FIGS. 5C-5D.
Figure 7A:
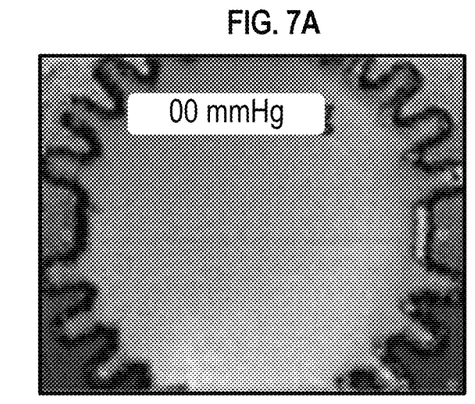
FIG. 7A is a top view of an optimal image depicting the diaphragm deflection of an improved capacitive pressure sensor, when the chamber pressure is 0 mmHg, according to one embodiment.
Figure 7B:
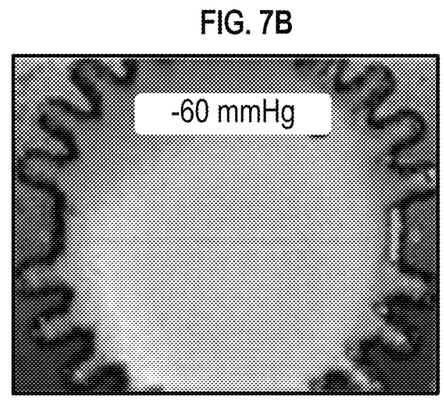
FIG. 7B is a top view of an optimal image depicting the diaphragm deflection of the improved capacitive pressure sensor of FIG. 7A, when the chamber pressure is −60 mmHg.
Figure 7C:
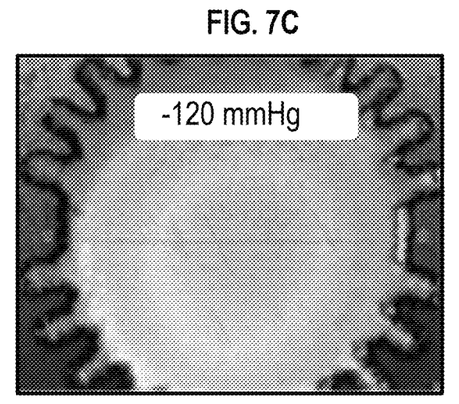
FIG. 7C is a top view of an optimal image depicting the diaphragm deflection of the improved capacitive pressure sensor of FIG. 7A, when the chamber pressure is −120 mmHg.
Figure 7D:
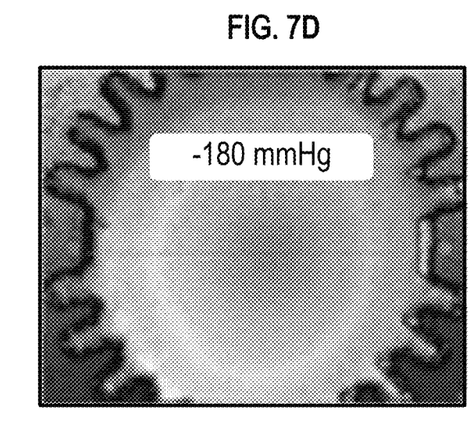
FIG. 7D is a top view of an optimal image depicting the diaphragm deflection of the improved capacitive pressure sensor of FIG. 7A, when the chamber pressure is −180 mmHg.
Figure 7E:
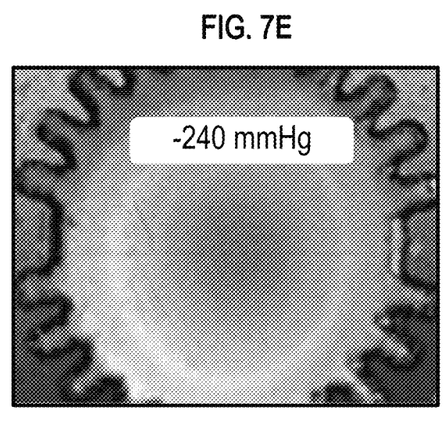
FIG. 7E is a top view of an optimal image depicting the diaphragm deflection of the improved capacitive pressure sensor of FIG. 7A, when the chamber pressure is −240 mmHg.
Figure 7F:
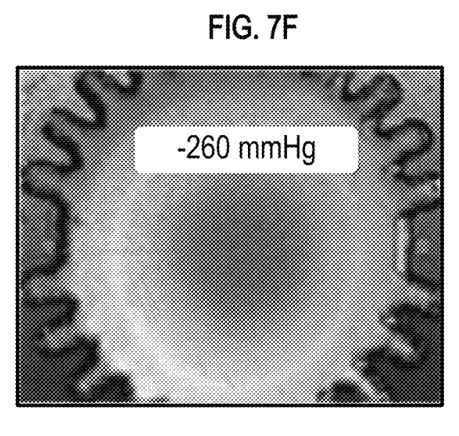
FIG. 7F is a top view of an optimal image depicting the diaphragm deflection of the improved capacitive pressure sensor of FIG. 7A, when the chamber pressure is −260 mmHg.

As examples, FIGS. 5A-5D compare the optical images of a conventional capacitive pressure sensor with a plain sidewall (FIGS. 5A-5B) (rarely succeeded in the formation because the diaphragm is prone to collapse) and an improved capacitive pressure sensor having a corrugated sidewall (FIGS. 5C-5D), and FIG. 6 compares the deflection behaviors of the diaphragms. In this experiment, an optical profilometer (Bruker, Contour GT) is used to measure the optical images and the diaphragm deflection profiles.

As shown, even when the diaphragm with the plain sidewall does not collapse (FIGS. 5A-5B), the diaphragm seriously bends downward and the sidewall bends inward (marked by solid arrows in FIG. 6) under zero pressure applied, resulting in a substantial deformation of the cavity chamber. For example, FIG. 6 marks the lateral boundaries a-a' of the upper edge of the plain sidewall, which bends inwardly and results in a smaller diameter than the diameter of the non-deflected diaphragm. By changing of the chamber pressure to −240 mmHg, the height of the sidewall for the plain cylindrical chamber is significantly reduced (by about 10%) along with the large downward deflection of the diaphragm, indicating that the plain sidewall is not strong enough to support the freestanding diaphragm (in this example, no data is shown in the region marked by small arrows due to the serious diaphragm deflection for plain sidewall sensor).

In contrast, the diaphragm with the corrugated sidewall (FIGS. 5C-5D) remains an almost flat surface, except a slight change near the edge. There is no observation of serious sidewall bending regardless of the applied pressure. For example, FIG. 6 marks the lateral boundaries b-b' of the upper edge of the corrugated sidewall, which generally maintains the original diameter of the non-deflected diaphragm. Thus, it further confirms that a degradation of the chamber sidewall is the major cause of the diaphragm collapses. Such degradation of the sidewall affects the functionality of diaphragm in the capacitive pressure sensor that requires the consistent deflection of diaphragm under the change of applied pressure.

Figure 8:
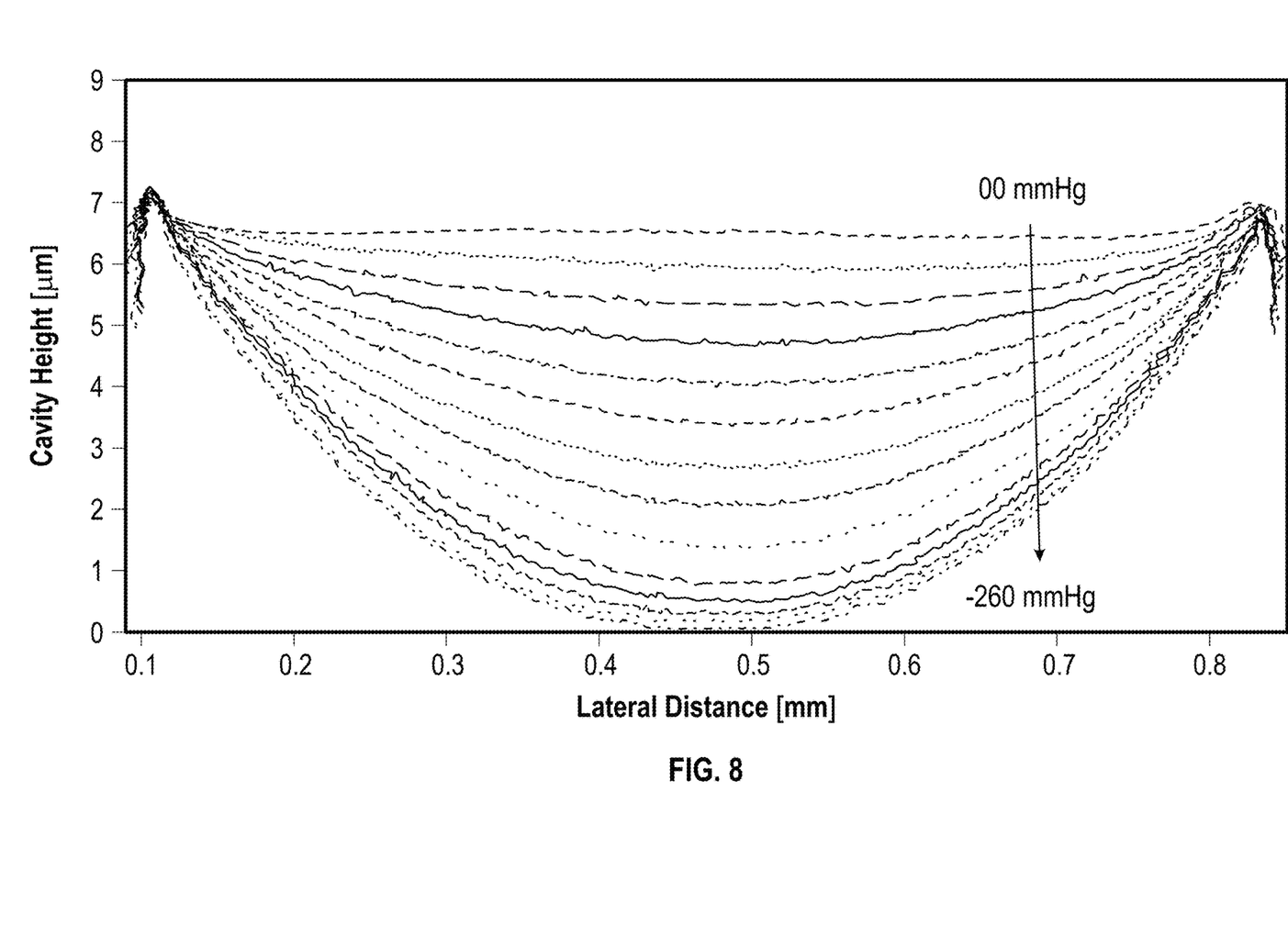
FIG. 8 is a plot comparing the diaphragm deflection behavior of the capacitive pressure sensor depicted in FIG. 7 under different pressure conditions.

FIGS. 7A-7F show optical images of an improved capacitive pressure sensor with a corrugated sidewall in operation as viewed from the top of the sensor. FIG. 8 shows the behavior of diaphragm deflection as a function of the applied pressure. In FIGS. 7A-7F, the varying greyscale in the optical images illustrate the deflection of the diaphragm at various pressures from 0 mmHg to −260 mmHg. As shown, the central portion of the diaphragm deflects more than the outer edge as the pressure applied thereto is increased, as illustrated by an increasingly larger and darker central portion of the diaphragm. For this specific example, the height of the corrugated wall (which defines the height of the cavity chamber when the diaphragm is not deflected) is about 7 µm to be sensitive in the range of pressure up to about 200 mmHg. It should be understood that different combination of the size of the diaphragm and height of the corrugated wall can lead to different sensor sensitivity for measuring the applied pressure. As shown in FIG. 8, the diaphragm deflection under different pressure loadings shows a monotonic behavior before it starts to touch the bottom (i.e., the base layer).

Figure 9:
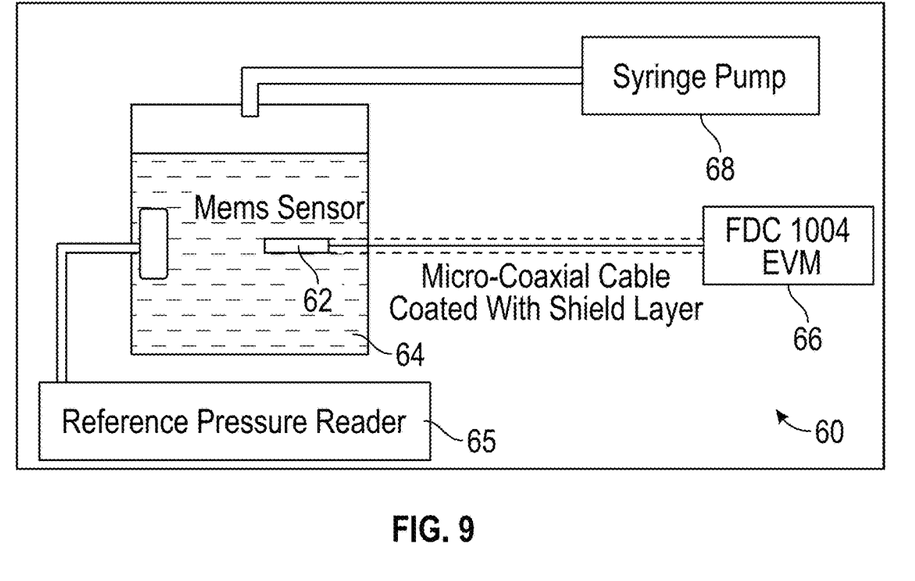
FIG. 9 is a schematic drawing illustrating an experimental setup to calibrate a fabricated pressure sensor.

The change of capacitance of the pressure sensor can be measured, for example, in water by an FDC1004 capacitance-to-digital converter (Texas Instrument). FIG. 9 shows one experimental setup 60 to calibrate the fabricated capacitive pressure sensor in water, according to one embodiment. As shown, a fabricated capacitive pressure sensor (with a corrugated wall) 62 can be fully immersed in water 64, and connected to a capacitance-to-digital converter 66. A reference pressure reader 65 can be used to measure the pressure at the sensor location and used for calibrating the sensor 62.

Figure 10:
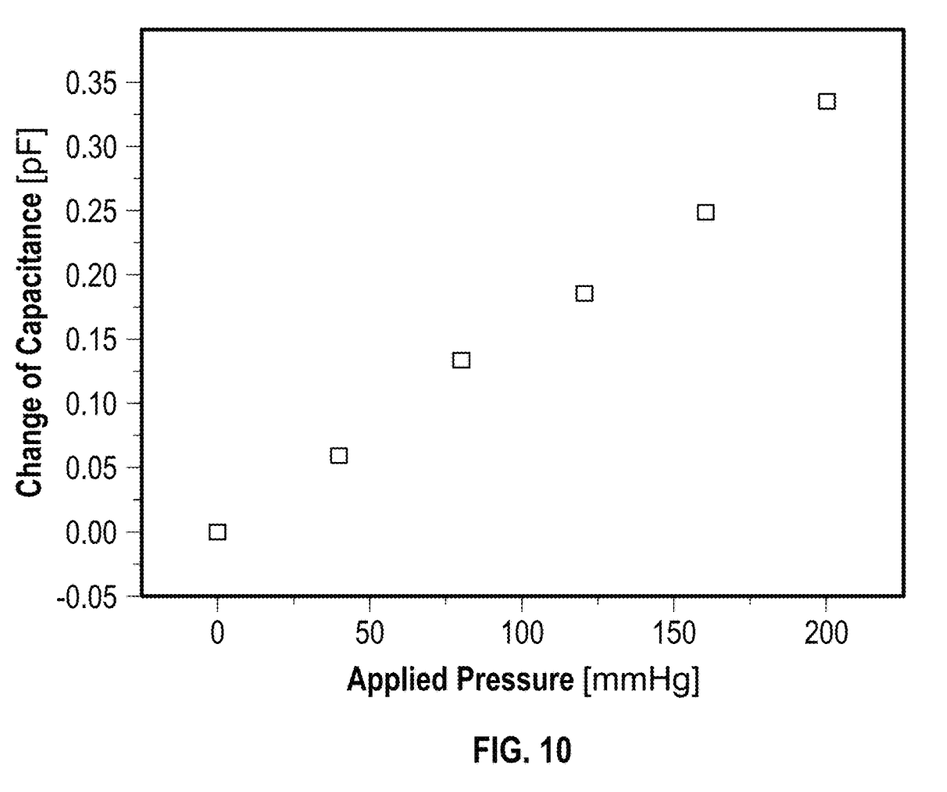
FIG. 10 is a plot depicting the calibration results obtained in an experiment.

In one experiment, as the water pressure was increased up to 200 mmHg, e.g., by pumping water from a syringe pump 68, the overall capacitance was changed to about 0.35 pF, showing a linear relationship between the capacitance and applied pressure as shown in FIG. 10. Thus, by adapting a corrugation pattern to the sidewall of the capacitive cavity chamber, the sidewall supporting the freestanding large diaphragm (e.g., 800 µm diameter) over the small cavity (e.g., 7 µm height) was strengthened. As a result, the diaphragm collapsing problem can be avoided or substantially resolved and the functionality in the diaphragm deflection can be enhanced as well. The fabricated sensor with the corrugation shows a linear relationship between the capacitance and applied pressure. In this specific experiment, it is shown that the overall capacitance change was 0.35 pF over the range of 200 mmHg in pressure, which is particular useful for the application of an implantable real-time blood pressure monitoring system, for example, as described in U.S. Publication No. 2016/0157868, which is incorporated herein by reference.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "connected" generally mean electrically, electromagnetically, and/or physically (e.g., mechanically or chemically) coupled or linked and does not exclude the presence of intermediate elements between the coupled or associated items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or," as well as "and" and "or."

As used herein, the term "approximately" and "about" means the listed value and any value that is within 20% of the listed value. For example, "about 200 mmHg" means any value between about 160 mmHg and about 240 mmHg, inclusive.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims.

The invention claimed is:

1. A sensor comprising:
   a deflectable diaphragm;
   a base layer opposite the diaphragm; and
   a corrugated wall extending between the diaphragm and the base layer;
   wherein the diaphragm is suspended over a cavity defined by the diaphragm, the base layer and the corrugated wall.

2. The sensor of claim 1, wherein the diaphragm comprises a first electrode and the base layer comprises a second electrode such that a capacitance between the first and second electrodes changes when the diaphragm is deflected relative to the cavity.

3. The sensor of claim 1, wherein the corrugated wall comprises a plurality of ridges alternating with a plurality of grooves.

4. The sensor of claim 1, wherein a ratio of a height of the corrugated wall to a diameter of the diaphragm ranges from about 0.0005 to about 1.

5. The sensor of claim 1, wherein the diaphragm has a diameter about 800 µm.

6. The sensor of claim 1, wherein the corrugated wall has a height about 7 µm.

7. The sensor of claim 2, wherein the first electrode is encapsulated between at least two parylene layers.

8. The sensor of claim 2, wherein the second electrode is encapsulated between at least two parylene layers.

9. The sensor of claim 3, wherein each of the plurality of ridges has a rectangle-shaped radial cross-section.

10. The sensor of claim 9, wherein the rectangle-shaped radial cross-section has a width about 80 µm and a length about 100 µm.

11. The sensor of claim 10, wherein two adjacent ridges form a radial angle about 15 degrees.

12. The sensor of claim 1, wherein the cavity is filled with a fluid, wherein the fluid has a dielectric constant greater than 1.

13. The sensor of claim 12, wherein the fluid comprises propylene carbonate.

14. A method of fabricating a sensor comprising:
forming a base layer on a substrate;
forming a corrugated wall on the base layer so as to form a cavity; and
forming a diaphragm suspended over the cavity and supported by the corrugated wall.

15. The method of claim 14, wherein the diaphragm comprises a first electrode and the base layer comprises a second electrode such that a capacitance between the first and second electrodes changes when the diaphragm is deflected relative to the cavity.

16. The method of claim 14, wherein the cavity is formed by removing a sacrificial photoresist layer deposited between the diaphragm and the base layer.

17. The method of claim 16, wherein the sacrificial photoresist layer is patterned to have a body portion having a corrugated side surface.

18. The method of 16 further comprising filling the cavity with a fluid, wherein the fluid has a dielectric constant greater than 1.

19. The method of claim 18, wherein filling the cavity with the fluid comprises submerging the base layer, the corrugated wall, and the diaphragm into a pool of the fluid for a predefined duration.

20. The method of claim 14 further comprises sealing the cavity.

\* \* \* \* \*